United States Patent [19]
Golinski et al.

[11] Patent Number: 4,596,551
[45] Date of Patent: Jun. 24, 1986

[54] TUBING CLAMP

[75] Inventors: Kenneth Golinski, Arlington Heights; Jimmy Miller, Waukegan; John Munsch, Libertyville, all of Ill.

[73] Assignee: Baxter Travenol Laboratories, Inc., Deerfield, Ill.

[21] Appl. No.: 558,137

[22] Filed: Dec. 5, 1983

[51] Int. Cl.⁴ ............................................. A61M 1/00
[52] U.S. Cl. ...................................... 604/29; 604/80; 604/410; 222/83; 141/330
[58] Field of Search ................... 604/80, 29, 30, 34, 604/280, 283, 905, 410-411; 128/DIG. 6, DIG. 26; 222/83; 141/330

[56] References Cited

U.S. PATENT DOCUMENTS

| | | | |
|---|---|---|---|
| 4,405,315 | 9/1983 | Handt | 604/411 |
| 4,413,988 | 11/1983 | Handt et al. | 604/29 |
| 4,439,193 | 3/1984 | Larkin | 604/905 |
| 4,460,358 | 7/1984 | Somerville | 604/34 |
| 4,473,369 | 9/1984 | Lueders et al. | 604/29 |
| 4,500,788 | 2/1985 | Kulin et al. | 604/29 |
| 4,541,829 | 9/1985 | Munsch et al. | |

FOREIGN PATENT DOCUMENTS

WO84/00895  3/1984  PCT Int'l Appl. ............... 604/408

Primary Examiner—Stephen C. Pellegrino
Assistant Examiner—Michelle Lester
Attorney, Agent, or Firm—Paul C. Flattery; Daniel D. Ryan; Garrettson Ellis

[57] ABSTRACT

A tubing clamp for firmly retaining flexible tubing without occluding flow through it and for forcing the tube into straight and open configuration. The tubing clamp rests on a platform member and comprises a pair of jaws positioned in opposed relation to each other and pivotally mounted on the platform member to be pivotally movable between open and closed positions. Facing surfaces of the jaws defines recesses that together define a tube port in the closed position of substantially the outer diameter of the tubing intended for retention therein. The tube has a parting line, and the jaws also define overlapping members at the parting line to prevent pinching of tubing occupying the tube port in the parting line as the jaws are moved to closed position.

18 Claims, 7 Drawing Figures

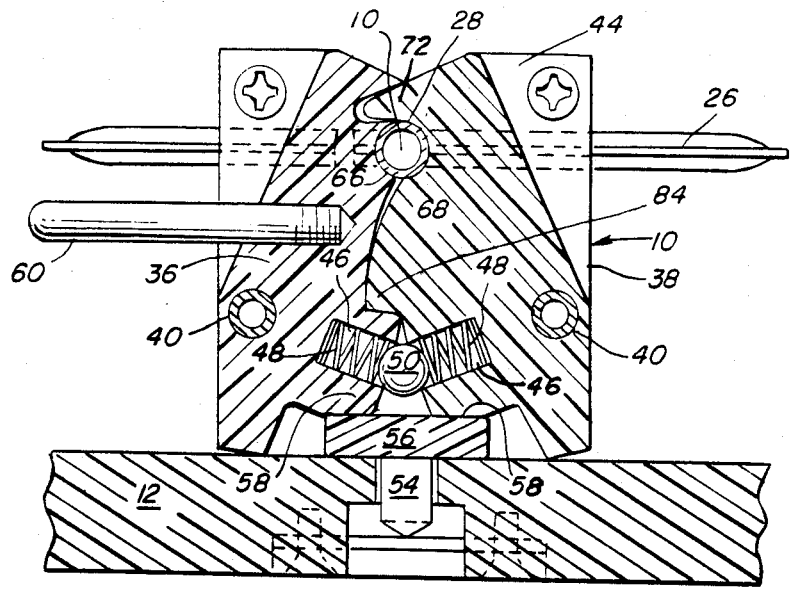
FIG. 3
FIG. 4
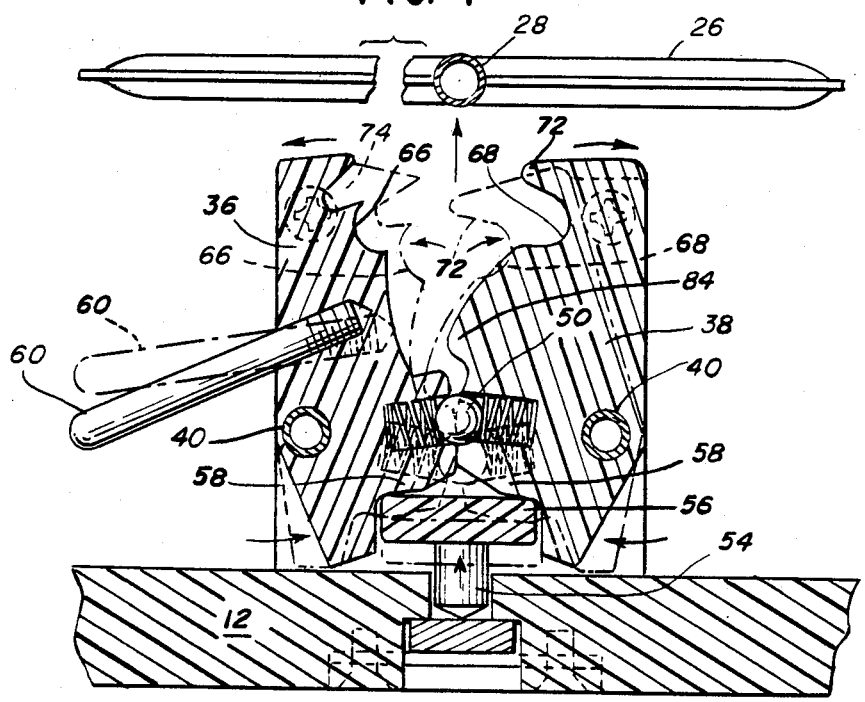

TUBING CLAMP

TECHNICAL FIELD AND PRIOR ART

In Munsch et al U.S. patent application Ser. No. 416,785, filed Sept. 10, 1982, now issued on a continuation application as U.S. Pat. No. 4,541,829 a device for automatic connection and disconnection is provided. The device is particularly used in the field of continuous ambulatory peritoneal dialysis, where extra effort must be exerted to maintain aseptic conditions during the course of the procedure, in which peritoneal dialysis solution is passed into the peritoneal cavity, and thereafter removed from the peritoneal cavity. This requires disconnection and reconnection of a connector which terminates tubing communicating with the interior of the peritoneal cavity to obtain and switch connection between various containers of peritoneal dialysis solution. The slightest touch of a critical portion of a connector with a contaminated surface is believed to create a significant risk of peritonitis to the patient.

Furthermore many peritoneal dialysis patients are debilitated by the underlying disease, having poor manual dexterity and muscular strength. The automatic exchange device can make it much easier for weakened peritoneal dialysis patients to make the connection. Many of them actually have difficulty in removing a spike connector, for example, from one bag port and putting it into another, lacking the physical strength.

A problem can exist with the device of the above-cited patent application. The spike connector which is being moved from one port tubing of a dialysis solution container to another port tubing of fresh dialysis solution container can sometimes miss its target, particularly in the case where the port tubing is flattened (not fully open) or bent out of line.

In accordance with this invention, a tubing clamp is provided for firmly retaining the flexible tubing without occluding flow through it, and for forcing the tube into a straight and open configuration, to greatly reduce or even eliminate the possibility that a "miss" can occur during an automatic connection exchange.

DESCRIPTION OF THE INVENTION

In accordance with this invention, the tubing clamp defines a pair of jaws positioned in opposed relation to each other and pivotally mounted on a platform member, to be pivotally movable between open and closed positions. Facing surfaces of the jaws each define recesses that together define a tube port in the closed position of substantially the outer diameter of the tubing intended for retention therein.

The jaws also define overlapping members at the parting line defined between the recesses that form the tube port. These overlapping members orient and prevent pinching of tubing occupying the tube port in the parting line as the jaws are moved to closed position. As the jaws move to closed position, the tubing is straightened and forced open to assume the shape of the tube port, so that the tubing is precisely and reliably positioned as a target for the automatically moved connector mounted in the automatic connection device.

The jaws may be spring-biased to urge movement out of all intermediate positions into either the open or the closed position, depending upon the exact intermediate position it moves out of. Specifically, the jaws may define facing ports, each containing a compressed coil spring, plus a ball member positioned between and abutting the outer ends of both springs, to provide the spring-biased movement.

Also, along both the top and the bottom of the parting line, the jaws may define overlapping members. An outer of the overlapping members is carried by one jaw, and is exposed to the front of the tubing clamp and fitting in a first recess of the other of the jaws in closed position. The other of the jaws may define an inner of the overlapping members spaced from the front of the tubing clamp and fitting in a second recess of the one jaw in closed position. This arrangement of overlapping members has been found to greatly reduce the problem of pinching of flexible tubing placed within the tube port for shaping and positioning.

The outer overlapping member and first recess may preferably be of less thickness than the inner overlapping member and second recess. Most preferably, the outer overlapping member and first recess are no more than one third as thick as the inner overlapping member and second recess. The first recess, being exposed to the front of the tubing clamp, if too deep, provides a place for the tubing to escape during the closing operation. This permits the tubing to move out of its desired position and shape. By causing the outer overlapping member and first recess to be substantially thinner than the inner overlapping member and second recess, this problem can be solved.

It is also preferable for the respective pivot means of the pivotally mounted jaws to be connected by strap means. This, plus preferably the arrangement of the compressed coiled springs and ball member described above, provides the desired snap-open and snap-closed action of the jaws. In the open position the ball member is desirably moved above the axis between the pivots, while in the closed position the ball member typically moves to a position below the axis between the pivots.

DESCRIPTION OF THE DRAWINGS

Referring to the drawings,

FIG. 3 is a longitudinal, sectional view of the tubing clamp of this invention as mounted in the apparatus of FIG. 1, the jaws being shown in the closed position.

FIG. 4 is a view similar to FIG. 3 but showing the jaws in open position.

DESCRIPTION OF SPECIFIC EMBODIMENT

Figure 1:
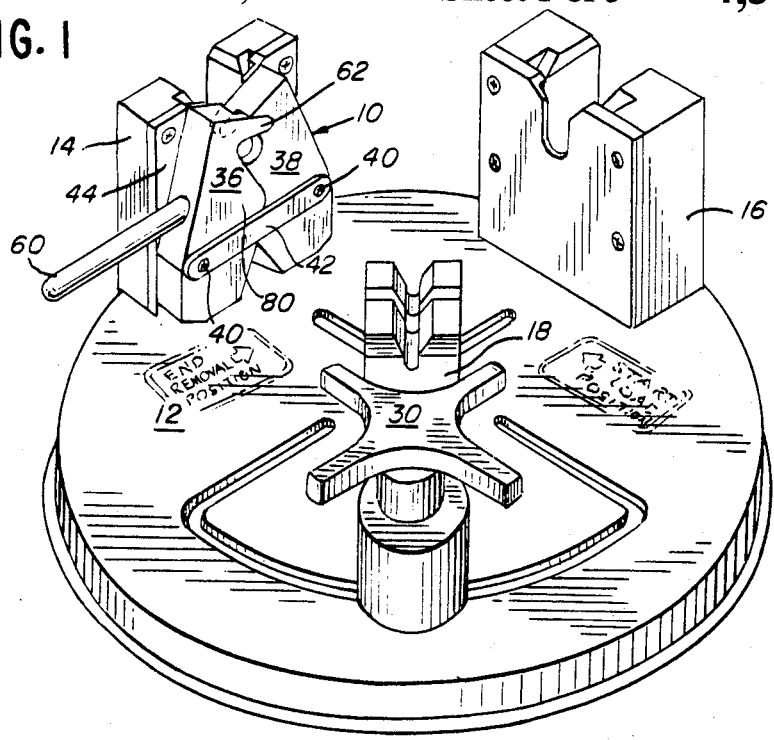
FIG. 1 is a perspective view of connection exchange apparatus using the tubing clamp of this invention.
Figure 2:
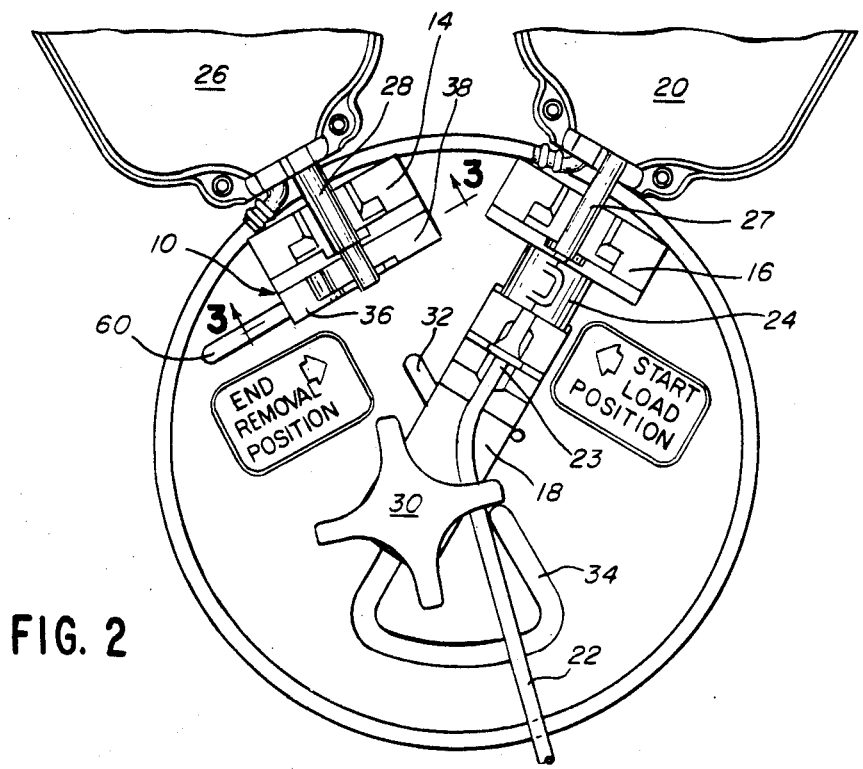
FIG. 2 is a plan view of the apparatus of FIG. 1.
Figure 5:
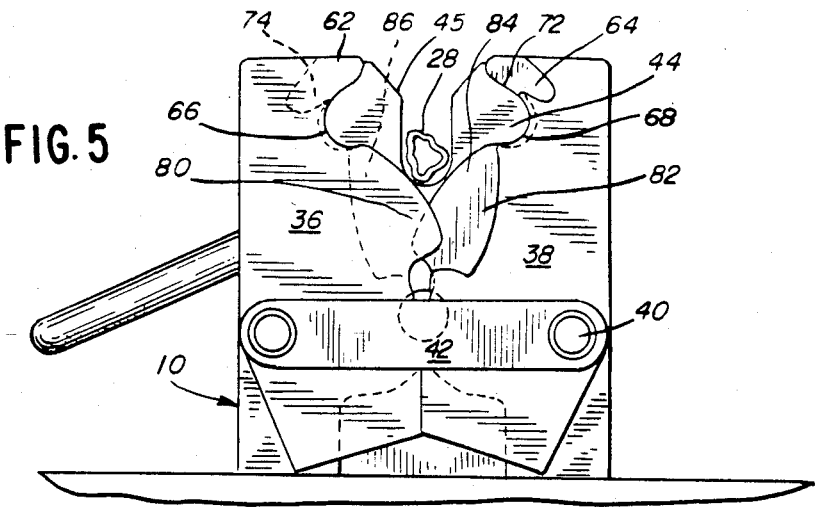
FIG. 5 is an elevational view of the tubing clamp of FIG. 4.

Referring to FIGS. 1 and 2, tubing clamp 10 is shown to be mounted on platform 12 by way of mounting block 14 as part of a connection exchange device which, except as otherwise shown, may be of the design disclosed in the previously cited Munsch et al U.S. application Ser. No. 416,785, filed Sept. 10, 1982, now issued on a continuation application as U.S. Pat. No. 4,541,829 or the Trav-X-change TM device, sold by Travenol Laboratories Inc. of Deerfield, Ill.

As shown, platform 12 also carries mounting block 16 and movable mounting member 18 for holding other connectors.

As FIG. 2 shows, mounting block 16 carries the container of spent peritoneal dialysis solution 20, which has been refilled with peritoneal dialysis solution from the peritoneal cavity through transfer set 22. Now it is desired to make an exchange by connector spike 23 on the end of transfer set 22 and enclosed in a conventional connection shield 24 (also sold by Travenol Laboratories) from its connection with bag 20 to a fresh peritoneal dialysis solution bag 26. To accomplish this, port 28 of bag 26 is placed into tubing clamp 10. Connection shield 24 is removed, and handle 30 is rotated, causing movable member 18, carrying spike 23 with it, to move along tracks 32, 34 by a rack and gear mechanism out of engagement with port 27 of bag 20 and into engagement with port 28, in a manner broadly similar to the currently available exchange device design described above, except as otherwise described herein.

Referring in greater detail to tubing clamp 10, jaws 36, 38 are mounted on mounting plate 44 by pivots 40, which may be rivets or the like. Pivots 40 are connected together by metal strap 42 to keep them in equidistant relation. Mounting plate 44 is mounted to mounting block 14, and defines slot 45, which is sufficiently narrow to prevent entry of the enlarged, distal portions of ports 28 of the current design of Travenol Laboratories, Inc. Thus the protector or cover for port 28 can be pulled off without allowing port 28 to advance through slot 45.

Jaws 36, 38 define facing ports 46, each containing a compressed coil spring 48. A ball member 50 is positioned between and abutting the outer ends of both springs 48, as shown in FIG. 3. As shown by comparing FIGS. 3 and 4, the above mentioned structures may be so positioned that ball 50 is in a position below an axis between pivots 40 in jaw-closed position, while ball 50 occupies a position above the axis between pivots 40 in the jaw-open position.

As in the previous embodiment commercially sold by Travenol, a push member 52 (FIG. 4) is carried by movable member 18, extending forwardly thereof on the underside of platform 12. Push member 52 can advance with member 18 to engage tapered post 54, pushing it and push plate 56 upwardly against shoulder members 58 of jaws 36, 38. Accordingly, as movable member 18 advances, the spike connector 23 that it carries advances into port 28. Then, push member 52 forces members 54, 56 upwardly, which in turn push shoulders 58 to cause jaws 36, 38 to rotate from the closed position of FIG. 3 to the open position of FIG. 4. This permits removal of spike 23 and port 28 from clamp 10. Jaws 36, 38 may then be manually closed, when desired, by manipulation of handle 60, after retraction of moving member 18 permits the dropping once again of members 54, 56. If desired, in this process another port of a fresh dialysis solution bag may be loaded into clamp 10. Cooperating action of springs 46, 48 and ball 50 transfers closing pressure from jaw 36 to jaw 38.

Push plate 56 extends laterally of push member 54 to shift the point of contact with each shoulder member 58 closer to each pivot 40. Thus less motion of members 56, 54 is required to open jaws 36, 38.

Jaw 36 defines an outer, overlapping member 62, which fits into corresponding first recess 64 on jaw 38. Overlapping member 62 is exposed to the front of tubing clamp 10 as shown in FIG. 1, as is recess 64, at least in the open position when not filled with overlapping member 62.

Each jaw member defines a recess 66, 68 (FIG. 4) which cooperate in the closed position to define tube port 70, shown to be cylindrical and of substantially the outer diameter or slightly less of port tubing 28 intended for retention therein. It can be seen that overlapping member 62 and recess 64 are located at the upper parting line between the jaw portions that define tube port 70.

The forward portion 71 of tube port 70 may have a slightly smaller diameter than the remainder of tube port 70, to focus the closing force of jaws 36, 38 there, to force tube 28 into round configuration. Typically, the front 0.08 inch of tube port 70 may have a ¼ inch diameter, while the remainder of port 70 has a diameter about 1/16 inch larger.

Similarly, jaw 38 defines an overlapping member 72, and jaw 36 defines a recess 74 to receive overlapping member 72 in jaw-closed position. Overlapping member 72 is an inner overlapping member, spaced from the front of tubing clamp 10 and fitting in second recess 74, which is located behind member 62.

Figure 6:
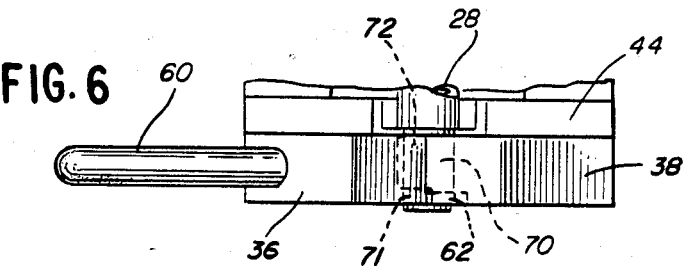
FIG. 6 is a fragmentary of plan view of the tubing clamp of FIG. 3.
Figure 7:
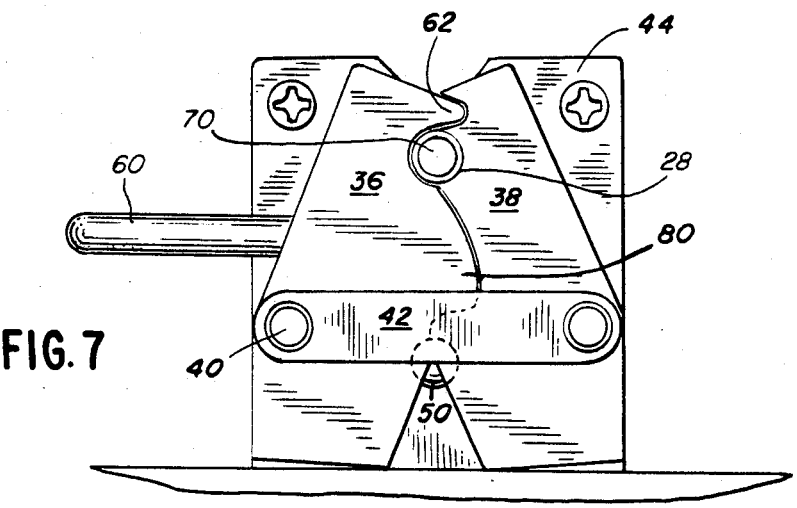
FIG. 7 is an elevational view of the tubing clamp of FIG. 3.

As shown in FIG. 6, the thickness of overlapping member 62 is less than one third of the thickness of overlapping member 72, with the corresponding thicknesses of recesses 64, 74 being in the same relationship to avoid a large, deep recess 64 into which tubings 28 may escape during the closing action, to avoid being precisely shaped and positioned in tubing port 70.

Each of overlapping members 62, 72 is a finger-like, projecting member to defining an arc of 140° or more. It is to be understood that by this definition an arc that is substantially a straight line would be of less than one degree, while an arc that causes the line to bend back into reverse, parallel relation such as the letter "U" is an arc of 180°. It can be seen the overlapping members 62, 72 define arcs of substantially over 90° typically but less than 180°.

The lower portion of the parting line that defines tube port 70 is also defined by overlapping members. Jaw 36 defines outer overlapping member 80, which fits into first recess 82 on jaw 38, as is the case with overlapping members 62, 64. Outer overlapping member 80 is exposed to the front side of tubing clamp 10, as is exposed recess 82 in the open position.

Jaw 38 defines inner overlapping member 84, which fits into second recess 86 on jaw 36. Second recess 86 is covered from the front exterior of tubing clamp 10 by outer overlapping member 80.

As before, outer overlapping member 80 and first recess 82 are less than one third the thickness of inner overlapping member 84 and second recess 86, to once again prevent tubing 28 from being able to lodge in first recess 82 in an out-of-line configuration from that desired.

The arcs defined by the edges of overlapping members 80, 82 can be seen to be less than 140°.

Accordingly, the tubing clamp of this invention can be used to firmly retain flexible tubing without occluding the flow through it, for forcing the tube into a straight and open configuration. This provides an opportunity for a great increase in the reliability of automated connection and disconnection devices, since the flexible tubing can be positioned as a target with precise positioning and predetermined cross-sectional configuration.

The above has been offered for illustrative purposes only, and is not intended to limit the scope of the invention of this application, which is as defined in the claims below.

That which is claimed is:

1. A tubing clamp for firmly retaining flexible tubing without occluding flow through it and for forcing said tube into a straight and open configuration, which comprises:

a platform member; a pair of jaws positioned in opposed relation to each other with each said jaw pivotally mounted on said platform member, said jaws being pivotally movable with respect to said platform between open and closed positions; facing surface of said jaws each defining recesses that together define a tube port in the closed position of substantially the outer diameter of the tubing intended for retention therein, said jaws also defining overlapping members at the parting line to prevent pinching of tubing occupying the tube port in the parting line as the jaws are moved to closed position.

2. The tubing clamp of claim 1 in which said jaws are spring-biased to urge movement out of all intermediate positions into one of said open and closed positions.

3. A tubing clamp for firmly retaining flexible tubing without occluding flow through it and for forcing said tube into a straight and open configuration, which comprises:

a platform member; a pair of jaws positioned in opposed relation to each other and pivotally mounted on said platform member to be pivotally movable between open and closed positions; facing surface of said jaws each defining recesses that together define a tube port in the closed position of substantially the outer diameter of the tubing intended for retention therein, said jaws also defining overlapping members at the parting line to prevent pinching of tubing occupying the tube port in the parting line as the jaws are moved to closed position; with said jaws being spring-biased to urge movement out of all intermediate positions into one of said open and closed positions and in which said jaws define facing ports, each containing a compressed coil spring, and a ball member positioned between and abutting the outer ends of both springs.

4. The tubing clamp of claim 1 in which, along both the top and bottom of the parting line, one of said jaws defining an outer of said overlapping members exposed to the front of said tubing clamp and fitting in a first recess of the other of said jaws in closed position; the other of said jaws defining an inner of said overlapping members spaced from the front of said tubing clamp and fitting in a second recess of said one jaw in closed position.

5. The tubing clamp of claim 4 in which each of the overlapping members at the top of the parting line defines an arc of greater than 140 degrees, and the overlapping members at the bottom of the parting line an arc of less than 140 degrees.

6. The tubing clamp of claim 4 in which said outer overlapping member and first recess are of less thickness than the inner overlapping member and second recess.

7. The tubing clamp of claim 6 in which the outer overlapping member and first recess are no more than one third as thick as the inner overlapping member and second recess.

8. The tubing clamp of claim 1 in which the pivotally mounted jaws are mounted on pivot means which are connected by strap means.

9. The tubing clamp of claim 8 in which one of said jaws defines a projecting handle for manual movement thereof.

10. A tubing clamp for firmly retaining flexible tubing without occluding flow through it and for forcing said tube into a straight and open configuration, which comprises:

a platform member, a pair of jaws positioned in opposed relation to each other, and pivotally mounted on said platform member to be pivotally movable between open and closed positions; facing surfaces of said jaws each defining recesses that together define a tube port in the closed position of substantially the outer diameter of the tubing intended for retention therein, said tube port having a parting line, said jaws also defining overlapping members at the parting line to prevent pinching of tubing occupying the tube port in the parting line as the jaws are moved to closed position, one of said jaws defining an outer of said overlapping members exposed to the front of said tubing clamp, and fitting in a first recess of the other of said jaws in closed position; the other of said jaws defining an inner of said overlapping members spaced from the front of said tubing clap and fitting in a second recess of said one jaw in closed position, said jaws being spring biased to urge movement out of all intermediate positions into one of said open and closed positions, said jaws defining facing ports, each containing a compressed coil spring, and a ball member positioned between and abutting the outer ends of both springs.

11. The tubing clamp of claim 10 in which each of the overlapping members at the top of the parting line defines an arc of greater than 140 degrees, and the overlapping members at the bottom of the parting line an arc of less than 140 degrees.

12. The tubing clamp of claim 10 in which the pivotally mounted jaws are mounted on pivot means which are connected by strap means.

13. The tubing clamp of claim 12 in which one of said jaws defines a projecting handle for manual movement thereof.

14. The tubing clamp of claim 13 in which said outer overlapping member and first recess are no more than one-third as thick as the inner overlapping member and second recess.

15. A tubing clamp for firmly retaining flexible tubing without occluding flow through it and for forcing said tube into a straight and open configuration, which comprises:

a platform member, a pair of jaws positioned in opposed relation to each other and pivotally mounted on said platform member, said jaws being pivotally movable between open and closed positions; facing surface of said jaws each defining recesses that together define a tube port in the closed position which is of substantially the outer diameter of the tubing intended for retention therein, said tube port having a parting line, said jaws also defining overlapping members at the parting line to prevent pinching of tubing occupying the tube port in the parting line as the jaws are moved to closed position, one of said jaws defining an outer of said overlapping members exposed to the front of said tubing clamp and fitting in a first recess of the other of said jaws in closed position; the other of said jaws defining an inner of said overlapping members spaced from the front of said tubing clamp and fitting in a second recess of said one jaw in closed position, said outer overlapping member and first recess being of less thickness than the inner overlapping member and second recess, said jaws being spring biased to urge movement out of all intermediate positions into one of said open and closed positions, the pivotally mounted jaws each being mounted on respective first or second pivot means which are connected by strap means.

16. The tubing clamp of claim 15 in which each of the overlapping members at the top of the parting line defines an arc of greater than 140 degrees, and the overlapping members at the bottom of the parting line an arc of less than 140 degrees.

17. The tubing clamp of claim 15 in which said outer overlapping member and first recess are no more than one-third as thick as the inner overlapping member and second recess.

18. The tubing clamp of claim 12 in which one of said jaws defines a projecting handle for manual movement thereof.

* * * * *